(12) United States Patent
Mower et al.

(10) Patent No.: US 7,964,234 B2
(45) Date of Patent: Jun. 21, 2011

(54) HIGH MINERAL CONTENT DIETARY SUPPLEMENT

(75) Inventors: Thomas William Mower, Elk Ridge, UT (US); Marlin Charles Harmon, Bountiful, UT (US); James Coats Bawden, Provo, UT (US); Daniel Ray Banks, Santaquin, UT (US); Joyce Jolene Young, Orem, UT (US)

(73) Assignee: Neways, Inc., Springville, UT (US)

( * ) Notice: Subject to any disclaimer, the term of this patent is extended or adjusted under 35 U.S.C. 154(b) by 303 days.

(21) Appl. No.: 11/173,611

(22) Filed: Jul. 1, 2005

(65) Prior Publication Data

US 2006/0093685 A1 May 4, 2006

Related U.S. Application Data

(60) Provisional application No. 60/622,879, filed on Oct. 28, 2004.

(51) Int. Cl.
*A61K 36/00* (2006.01)
(52) U.S. Cl. ......... 426/648; 426/590; 426/599; 424/725
(58) Field of Classification Search .................. None
See application file for complete search history.

(56) References Cited

U.S. PATENT DOCUMENTS

| | | | |
|---|---|---|---|
| 2,761,783 A | 9/1956 | Ferguson, Jr. | |
| 3,011,897 A | 12/1961 | Grosvenor, Jr. | |
| 4,084,010 A | 4/1978 | Takemoto et al. | |
| 4,408,041 A | 10/1983 | Hirao et al. | |
| 4,690,827 A | 9/1987 | Kupper et al. | |
| 4,717,765 A | 1/1988 | Hirao et al. | |
| 4,725,387 A | 2/1988 | Hirao et al. | |
| 4,758,660 A | 7/1988 | Takeuchi et al. | |
| 4,789,559 A | 12/1988 | Hirao et al. | |
| 4,870,059 A | 9/1989 | Mitsuhashi et al. | |
| 4,917,916 A | 4/1990 | Hirao et al. | |
| 5,225,221 A * | 7/1993 | Camden et al. | 426/74 |
| 5,411,755 A | 5/1995 | Downton et al. | |
| 5,433,961 A | 7/1995 | Lanner et al. | |
| 5,433,965 A * | 7/1995 | Fischer et al. | 426/548 |
| 6,103,240 A | 8/2000 | Zhou | |
| 6,124,442 A | 9/2000 | Zhou et al. | |
| 6,299,925 B1 | 10/2001 | Xiong et al. | |
| 6,387,370 B1 | 5/2002 | Yegorova | |
| 6,413,558 B1 | 7/2002 | Weber et al. | |
| 6,416,806 B1 | 7/2002 | Zhou | |
| 6,582,753 B1 * | 6/2003 | Willibald-Ettle et al. | 426/660 |
| 7,014,872 B2 | 3/2006 | Pushpangadan et al. | |
| 2002/0068102 A1 | 6/2002 | Su et al. | |
| 2002/0090406 A1 | 7/2002 | Su et al. | |
| 2002/0132037 A1 | 9/2002 | Zhou | |
| 2005/0085454 A1* | 4/2005 | Ghosal | 514/185 |

FOREIGN PATENT DOCUMENTS

| | | |
|---|---|---|
| JP | 10 52-57366 | 5/1977 |
| JP | 52-83986 | 7/1977 |
| JP | 52-143257 | 11/1977 |
| JP | 356117781 A | 9/1981 |
| JP | 56-158072 | 12/1981 |
| JP | 57-86266 | 5/1982 |
| JP | 58-36368 | 3/1983 |
| JP | 58071868 | 4/1983 |
| JP | 358116674 A | 7/1983 |
| JP | 6012074 | 7/1985 |

OTHER PUBLICATIONS

Your Healthy World: Maximol Solutions Food Supplement; online, URL <http://www.yourhealthyworld.com/acatalog/Maximol.html>, pp. 1-3.*
Your Healthy World: Maximol Solutions Food Supplement; online, URL <http://www.yourhealthyworld.com/acatalog/Maximol.html>, embedded pop-up link, p. 1.*
PR Newswire; Neways' Top-Selling Supplement Launched With Improved Benefits; New York, Jan. 5, 2004, p. 1 (pp. 1-2 of print-out from ProQuest online Database).*
Product label No. 1111/1 for the dietary supplement Maximol Solutions, which was never printed.
Product label No. 1111/2 for the dietary supplement Maximol Solutions (circa 2001).
Product label No. 1111/3 for the dietary supplement Maximol Solutions (circa 2004).
U.S. Appl. No. 10/612,754, filed Jul. 1, 2003, Mower et al.
U.S. Appl. No. 11/459,322, filed Jul. 21, 2006, Mower et al.
Office Action dated Jan. 23, 2009 from U.S. Appl. No. 10/612,754, 21 pages.
Office Action dated Jul. 22, 2008 from U.S. Appl. No. 10/612,754, 21 pages.
Office Action dated Jan. 4, 2008 from U.S. Appl. No. 10/612,754, 21 pages.
Office Action dated Apr. 6, 2007 from U.S. Appl. No. 10/612,754, 21 pages.
Office Action dated Oct. 10, 2006 from U.S. Appl. No. 10/612,754, 15 pages.
Office Action dated Apr. 29, 2010 from U.S. Appl. No. 11/459,322.

* cited by examiner

*Primary Examiner* — Patricia Leith
(74) *Attorney, Agent, or Firm* — Workman Nydegger

(57) ABSTRACT

Liquid dietary supplements include vitamins, macro minerals, trace minerals, high Oxygen Radical Absorption Capacity (ORAC) compounds, and optionally fulvates. Despite the tendency of minerals in such a liquid mineral and vitamin supplement to precipitate and for the ingredients to quickly degrade, particularly at high ORAC values and low pH, embodiments of the invention stay in solution have a desired shelf life without degrading. In part, this is achieved through the use of the natural preservative Momordica, carefully formulated amounts of the various ingredients, and high-tech processing.

19 Claims, No Drawings

HIGH MINERAL CONTENT DIETARY SUPPLEMENT

CROSS-REFERENCE TO RELATED APPLICATIONS

This application claims the benefit of U.S. Provisional Application No. 60/622,879, filed Oct. 28, 2004, which is incorporated by reference herein in its entirety.

BACKGROUND OF THE INVENTION

1. The Field of the Invention

The present invention relates generally to dietary supplements. More particularly, the present invention relates to dietary supplement formulations that incorporate minerals, antioxidants, vitamins, and other ingredients in a dietary supplement having a long shelf life, high ORAC values, and good mineral solubility.

2. The Relevant Technology

The field of dietary supplements and nutraceuticals has exploded in recent years as scientific discoveries and public awareness campaigns have brought the health benefits of numerous dietary supplements to the consuming public's general awareness. Among the more popular forms for these dietary supplements are vitamin supplements, mineral-based supplements, and antioxidants.

Vitamin supplements are perhaps the most well-known and widely used dietary supplements. Vitamins are generally defined as organic substances that are essential to normal bodily metabolism, insufficient amounts of which in the diet can cause significant vitamin deficiency diseases. Vitamin supplements address the risk of deficiencies by including either specific vitamins, such as vitamin B, vitamin C, and vitamin E, or combinations of the individual vitamins in "multivitamins" that include up to dozens of the foregoing and other vitamins or supplements. The dosages of each vitamin in vitamin supplements range from small amounts, often a recommended daily value, to larger amounts when permitted by regulations. The amount of vitamins that are actually absorbed into the body as opposed to merely passed through the digestive tract, however, is subject to debate. Studies suggest that significant amounts of consumed vitamins are not absorbed and are therefore not of utility to the consumer.

Similarly, mineral supplements are also well known and widely consumed. In contrast to vitamins, which are organic substances, minerals, as they pertain to human nutrition, are inorganic chemical substances that are necessary to proper bodily function. Many minerals are required in small amounts for proper enzymatic function (and in the case of calcium, phosphorus, and other minerals, structural function) of the body. As with vitamins, deficiency of one or more minerals can cause a serious dysfunction of bodily systems. Examples of required minerals are calcium, chloride, magnesium, phosphorus, potassium, sulfur and sodium. As used herein, the term "macro minerals" refers to those minerals that are widely known to be required for bodily function and that we need in the largest quantity.

The use of antioxidants in dietary supplements to improve bodily health is also increasingly prevalent. Generally, an antioxidant is a chemical which combines with free radicals and/or other chemicals that release free radicals that would otherwise attack molecules in the body, and abnormally oxidize them. Molecules that have been identified as susceptible to oxidants (and therefore may be protected by antioxidants) include DNA, RNA, lipids, and proteins. Examples of antioxidants include vitamins A, C, E, B-1, B-5, B-6, the amino acid cysteine, the food antioxidants BHT and BHA, and the minerals selenium and zinc.

Combinations of antioxidants are often found in relatively high levels in naturally occurring compounds. Such compounds that are touted as having an antioxidant effect are often measured in terms of their Oxygen Radical Absorption Capacity (ORAC) value, which measures their antioxidant capacity. Typically, fruits with an ORAC value of greater than 1000 ORAC Units per 100 gm of fruit are considered to have a high ORAC value. For that reason and others, fruit juices are often included in dietary supplements.

Other dietary supplements include "trace minerals" and/or filvates. As used herein, the term "trace minerals" denotes those minerals that are required in much smaller amounts than the afore mentioned macro minerals, and are therefore often omitted from mineral supplements. In addition to specific function in human metabolism, trace minerals are often touted for conditioning the body for more ready absorption of other necessary food intakes, such as vitamins.

Although the distinction between the "macro minerals" and "trace minerals" can be blurry, trace minerals typically include within their scope numerous elements, including among others: boron, chromium, cobalt, copper, fluoride, iodine, lithium, manganese, molybdenum, nickel, selenium, tin, and vanadium.

Fulvates are highly active electrolytes created in symbiotic relationship with tiny soil microbes which help break down insoluble minerals and organic material to make it available again for use by living plants. Scientists postulate that fulvates also play a vital role in providing essential nutrients and trace minerals for use by the human body, turning inorganic mineral elements into readily absorbable and bioavailable charged nutrients. It is believed that after transporting their load of ionized minerals and nutrients to body cells where they can be converted into energy, fulvates exit the cells. As they exit, they bind to any toxic heavy metals that may exist in the cytoplasm of the cell. Fulvates also transport nutrients into cells, where they can be eliminated as waste from the body. Thus, it is believed that fulvates serve a dual role within the body—they deliver electrical energy, minerals and other nutrients to the body and clear out toxins, energy depleted nutrients and exhausted minerals from the cell.

Because each of the foregoing, vitamins, macro minerals, trace minerals, high ORAC compounds, and fulvates, are of great interest to consumers interested in increasing their health through the consumption of dietary supplements, it would represent an advance to provide supplements that include many of the foregoing in a single dietary supplement.

Recent scientific research, however, has led to the realization that the amount of active ingredients, including vitamins, macro minerals, trace minerals, high ORAC compounds, and fulvates, in a dietary supplement diminishes over time. This happens as the product degrades. Therefore, the amount of a particular ingredient (or its activity) that is listed on a product label may be increasingly less accurate over time. For that reason, the United States Government has issued regulations that require labels to reflect what is in a product at a given time as opposed to what ingredients are simply added as the product is prepared.

Preparing formulations of dietary supplement that include vitamins, macro minerals, trace minerals, high ORAC compounds, and filvates, and that maintains the listed levels of ingredients, is not a simple task. High acidity, mineral activity, antioxidant activity, and other aspects of these ingredients can cause one or more of the ingredients to quickly break down leading to a very short product shelf life. It would therefore represent an advance in the field of dietary supplements to provide a supplement that combines vitamins, macro minerals, trace minerals, high ORAC compounds, and/or fulvates in a single product with a long shelf life.

In addition, one common problem with liquid mineral supplements is the tendency for the minerals to precipitate out of solution. Although this may not cause a significant problem in terms of nutritional value for a consumer, it can be unsightly or unpleasant for consumption. It would therefore also present an advance in the art to provide a supplement that combines vitamins, macro minerals, trace minerals, high ORAC compounds, and/or fulvates in a single product with good long term mineral solubility.

BRIEF SUMMARY OF THE INVENTION

The present invention relates to liquid dietary supplements that include vitamins, macro minerals, trace minerals, high Oxygen Radical Absorption Capacity (ORAC) compounds, and optionally filvates, as well as other optional ingredients. Despite the tendency of minerals in such a liquid mineral and vitamin supplement to precipitate and for the ingredients to quickly degrade, particularly at high ORAC values and low pH, embodiments of the invention stay in solution and have a desired shelf life without degrading. In part, this is achieved through the use of the natural preservative *Momordica grosvenori* extract. Precise processing, including ultra high temperature pasteurization, helps preserve the dietary supplements as well.

According to a first example embodiment of the invention, a liquid mineral and vitamin dietary supplement includes: vitamins, minerals, high-ORAC fruit juice(s), and water, wherein the blend is formulated and prepared such that the minerals and vitamins do not precipitate out of the liquid supplement; and *Momordica grosvenori* in an amount sufficient to inhibit bacterial growth in the liquid supplement and thereby extend shelf life. The liquid supplement has pH and ORAC levels that are known to break down one or more ingredients of the supplement such that the shelf life of the blend would be less than desired and wherein the liquid supplement is formulated and processed such that the shelf life of the supplement is as desired.

Another example embodiment of the invention is an aqueous antioxidant, fulvate enhanced, mineral and vitamin dietary supplement that has a pH of from about 2.3 to about 3.9 and an ORAC value of from about 500 to about 10,000µmole Trolox equivalents (TE) per 100gm. The dietary supplement includes: from about 0% to about 2% by dry weight vitamins; from about 0% to about 7% by dry weight macrominerals comprising compounds including minerals selected from the group consisting of calcium, chloride, magnesium, phosphorus, potassium, sulfur and sodium; at least about 0.01% by dry weight of a trace mineral composition; one or more high-ORAC fruit juice(s) and/or high-ORAC fruit extracts from about 0.01 to about 5% by wet weight; at least about 0.01% by dry weight fulvates; and from about 0 to about 1% by dry weight *Momordica*. The dietary supplement is formulated and prepared such that the fulvates, minerals and vitamins do not precipitate out of the dietary supplement and such that the shelf life of the supplement is at least about 2 years.

These and other objects and features of the present invention will become more fully apparent from the following description and appended claims, or may be learned by the practice of the invention as set forth hereinafter.

DETAILED DESCRIPTION OF THE PREFERRED EMBODIMENTS

The present invention relates to a dietary supplement having a relatively long shelf life that includes vitamins, macro minerals, trace minerals, high Oxygen Radical Absorption Capacity (ORAC) compounds, and fulvates. Preferred embodiments will include each of the foregoing, although it is anticipated that certain embodiments of the invention may omit one or more of them.

In the following description, numerous specific details are set forth in order to provide a thorough understanding of the present invention. It will be obvious, however, to one skilled in the art that the present invention may be practiced without these specific details. In other instances, well known aspects of dietary supplements have not been described in particular detail in order to avoid unnecessarily obscuring the present invention. Concentrations of each of the components of the dietary supplements are presented in their preferred form which typically includes a certain percentage of water. One skilled in the art will recognize that it is a simple matter to account for the water in determining the effective amount of the ingredient that is present in a recited concentrate.

As used herein, the term "shelf life" shall refer to the length of time a dietary supplement will last without deteriorating. More particularly, the term "shelf life" shall indicate both the length of time that a dietary supplement is fit for human consumption and has a measurable formulation that matches the product labeling within an FDA recommended series of stability testing as set forth in the United States Pharmacopeia (USP).

For consumption, dietary supplements according to the invention are typically designed to be consumed in small doses, for example one-half ounce once twice daily on an empty stomach. The dietary supplements may optionally be mixed with a diluent such as juice for consumption as well.

The dietary supplements are prepared by a variety of processing techniques known in the field of liquid food preparation, including for example ultra-high temperature (UHT)/short period of contact pasteurization. As optionally implemented in preparing dietary supplements according to the invention, ultra-high temperature (UHT)/short period of contact involves heating a liquid blend to about 285° F. for a period of about five seconds. The blend is then chilled very quickly. This combination of rapid heating and cooling kills bacteria and other microbes, but avoids damaging the ingredients in the dietary supplement.

A. Composition

1. Macro Minerals

Minerals for human needs can be separated based on the amount that we need. As previously noted, the minerals that we need in the largest quantity (hundreds of milligrams per day) are called "macrominerals." Macrominerals are minerals with a recommended daily allowance greater than 100 mg per day. These minerals also make up at least 0.01 percent of total body weight in humans. In contrast, essential trace minerals and microminerals are minerals needed in quantities of less than 100 mg per day.

Macrominerals as a group is generally defined to include seven important minerals: calcium, chloride, magnesium, phosphorus, potassium, sulfur and sodium. The human body will not function properly if any one of the seven is missing or deficient. The human body regulates its mineral balance by washing out excess minerals or absorbing additional minerals during digestion. Nevertheless, mineral deficiencies can occur depending upon a person's age, genetic disposition, or dietary deficiency. For example, many people over the age of 50 are likely to be deficient in calcium because they are not able to absorb as much minerals from normal food sources as when they were younger. Since we can not generate these minerals ourselves, the only source for us to get them into our body is by consuming them, either in everyday food or in supplements. For these and other reasons, the inclusion of macro minerals in dietary supplements helps ensure that consumers get an adequate supply of essential macro minerals.

Preferred compositions to administer several of these macro minerals in embodiments of the invention include, by way of example only: calcium lactate, calcium chloride, magnesium chloride, potassium citrate, and potassium chloride.

2. Trace Minerals

The minerals that we need in lesser quantities than macro-minerals are herein called "trace minerals." Although the required quantity of these trace minerals for bodily processes is less than that for macro minerals, deficiencies are nevertheless still harmful. For example, many people are likely to be deficient in iron, manganese, and zinc. Trace minerals may include, for example: Chromium, Copper, Iodine, Iron, Manganese, Molybdenum, Selenium, Zinc, Boron, Cobalt, Dysprosium, Erbium, Europium, Fluoride, Gadolinium, Gallium, Germanium, Gold, Hafnium, Holmium, Indium, Iridium, Lanthanum, Lithium, Lutetium, Molybdenum, Neodymium, Nickel, Selenium, Silicon, Silver, Strontium, Sulfur, Tantalum, Tellurium, Terbium, Thallium, Thorium, Thulium, Tin, Titanium, Tungsten, Vanadium, Ytterbium, Yttrium, Zinc, and Zirconium. The relative benefits and necessity of each of these trace minerals is well documented and will not be described in detail herein.

Trace minerals can often be advantageously found in nature in a highly concentrated source in a similar proportion as healthy, living matter. Accordingly, embodiments of the invention may include trace minerals in the form they were collected in nature. For example, one source of trace minerals comes from deposits surrounding the Great Salt Lake. This supply of minerals was created in the proper ratios by living organisms that became part of the fossilized mineral-rich earth known as the Ancient Lake Bonneville. Alternatively, the trace minerals can be provided in a prepared mineral powder. Such a powder may include, for example, one or more of the foregoing macro and/or trace elements as well as other desired additives.

In addition to individual benefits trace minerals provide to the body, trace minerals may also condition the body for more ready absorption of the other ingredients.

3. Vitamins

As previously noted, various vitamins can be included as components in the herein disclosed dietary supplements. The selection of specific vitamins in the herein disclosed dietary supplements may vary and the concentrations of them may range from small amounts, often a recommended daily value, to larger amounts. By way of example only, compatible compositions used to administer vitamins in the herein disclosed dietary supplements include: ascorbic acid (vitamin C); Biotin; cyanocobalamin (vitamin B12); niacinamide (niacin); thiamin mononitrate (vitamin B1); riboflavin (vitamin B2); pyridoxine hydrochloride (vitamin B6); folic acid; and d-calcium pantothenate (pantothenic acid).

4. Antioxidants

Embodiments of the invention also include antioxidants from various sources. Antioxidants are substances that function by neutralizing free radical molecules, which are responsible for oxidation and have been linked to aging and disease. By way of example only, embodiments of the invention can include high antioxidant levels from multiple sources, including raspberry and blueberry concentrates, strawberry, elderberry, orange, and green tea extracts, as well as from a specific formulation designed to provide a high ORAC value to a composition. Each added extract or formulation possesses a high Oxygen Radical Absorbance Capacity (ORAC) value, a value determined from a standardized assay or test that measures free radical-scavenging ability, or antioxidant potential. High ORAC values indicate a greater ability to absorb free radicals. ORAC values are determined using well-defined Trolox equivalence methods.

Typically, fruits with an ORAC value of greater than 1000 ORAC Units (μmole Trolox equivalence (TE) per 100 gm) of fruit are considered to have a high ORAC value. For reference, equivalent amounts of several juices were measured for antioxidant values. One hundred percent orange juice (100 gm) was measured to have an ORAC value of 2,400.0 100% blueberry juice has an ORAC value of 6,100.0, and 100% black raspberry juice has an ORAC value of 16,400.00. Embodiments of the invention, in contrast, have been measured to have ORAC values as high as 48,800 (μmole Trolox equivalence per 100 gm).

Common preferred fruits are raspberry and blueberry, which are effective antioxidants and thereby provide increased cellular health. Other preferred fruit concentrates having a high ORAC value include, by way of example only, grapes, blackberries, strawberries, plums, oranges, cherries, and kiwi fruits, currants, elderberries, black currants, cranberries, acai, and others that are well known in the art. Various of the fruit juices that are acceptable for use in the dietary supplements of the present invention, such as raspberry and blueberry, are commercially available from the natural juice company Ocean Spray, located in Prosser, Wash.

Particularly, blueberry extracts are potent antioxidants due largely in part to the flavonoids found therein. Generally, over 4,000 different flavonoids have been identified, of which approximately 150 have been extensively studied. It is known that blueberries contain high concentrations of one subclass of flavonoids, the darkly colored anthocyanins. One anthocyanin, theaflavin, gives blueberries their deep blue color. Blueberry anthocyanins now appear to be the most powerful antioxidants among flavonoids. In addition to their antioxidant properties, anthocyanins are also able to neutralize certain destructive enzymes such as metalloproteinases, initiate anti-inflammatory effects on blood vessels, inhibit serum protein decreases induced by hyperoxia, assist the body in dissolving blood clots, and exhibit anticancer effects not directly related to reactive oxygen species (ROS).

ROS leads to chronic human diseases. Antioxidant interference with oxidization of low-density lipoproteins (LDL) has been firmly established as a major retardant of cardiovascular disease. For example, one study suggested that anthocyanins are the key component in red wine that protects against cardiovascular disease rather than the commonly theorized active constituent, resveratrol.

In the last few years, many other chronic diseases have been linked to free-radical induced cellular damage. Additionally, it has been shown that fruit antioxidants can reverse some age-related neuronal/behavioral dysfunctions in animal models, increase dexterity and other motor skills, and increase cognition. Anthocyanins found in fruits and vegetables are as effective in the normalization of neuronal aging and behavior as they are in the prevention of carcinogenesis and cardiovascular disease.

More recent studies have shown that blueberry anthocyanins are more bioavailable than most other antioxidants. Many antioxidants do not reach therapeutic levels in plasma or tissues because they cannot penetrate and cross cell membranes. However, anthocyanins penetrate physiologic barriers, including the central nervous system, more effectively than other antioxidants. Anthocyanins linger in the body and are not rapidly metabolized, thus leading to longer lasting therapeutic effects.

Other conditions where anthocyanins have shown promising results are: 1) stroke; 2) capillary damage due to diabetic vascular disease; 3) hypertensive vessel damage; 4) arthritic or muscle conditions involving damaged collagen and/or elastin; 5) other inflammatory conditions associated with prostaglandins; 6) immune cell function; and 7) treatment of urinary tract infections. More inclusively, oxidative damage can be observed within every class of bio-molecule, including nucleic acids, proteins, lipids, and carbohydrates. Although much of the possible oxidative damage is not directly attributable to a primary mechanism (as seen in over-eating or intense exercise), it is often secondary to excessive oxidative stress resulting from beta-amyloid-induced free radicals, mitochondrial abnormalities, inadequate energy supply, inflammation, or altered antioxidant defenses.

Blueberries are preferably supplied as a concentrate in a 7:1 or 8:1 water:blueberry ratio based upon current supplier preferences. Of course, equivalent amounts of blueberries can be supplied in other forms, such as juice, powder, freeze dried, etc. Blueberries are preferably supplied in embodiments of the invention as a frozen concentrate having a 7:1 or 8:1 water:blueberry ratio based upon current supplier preferences. Blueberry fruit juice concentrate is preferably included in the dietary supplements according to the invention in a range by wet weight of from about 0 percent to about 5 percent, more preferably from about 1 percent to about 3 percent.

Another preferred high-ORAC fruit juice, raspberry juice, also has a wide variety of flavonoids. In addition, since raspberries contain unique anthocyanin flavonoids (ellagitannins, kaempferol, procyanidin, and quercetin, it is an ideal part of a multicomponent antioxidant system. Recently, researchers found that procyanidins block cell cycle at the G2/M phase, thereby providing anti-tumor activity. The same research also noted that procyanidins block key enzymes in polyamine synthesis, thus slowing tumor growth. Others have concluded that raspberries in orally available doses have the ability to prevent cataract formation. These researchers theorized that the mechanism of eye protection was due to a unique antioxidant effect.

In addition, raspberries provide an extremely high concentration of the natural anti-mutagen ellagic acid. Ellagic acid offers unique health benefits unrelated to its antioxidant potential. More than 125 studies done with Ellagic acid have demonstrated the efficacy of this natural food acid. The following is a brief compilation of effects seen with raspberry and/or ellagic acid documented in these studies: 1) an ability of ellagic acid to modulate gene expression in prostate cancer cell cultures; 2) inhibition of liver cancer cells by multiple mechanisms; 3) inhibition of multiple enzyme systems that promote bladder cancer cell growth; 4) protection of the colon mucosa leading to prevention of pre-cancerous cell formation; 5) inhibition of chemically induced esophageal cancer; 6) inhibition of chemically-induced lung tumors; 7) activity against leukemic cells in vitro; and 8) inhibition of chemically-induced skin carcinoma in mice.

Other unique cellular effects of ellagic acid and/or raspberry are: 1) protection of the stomach mucosal lining through multiple mechanisms; 2) protection of the colon lining against colitis type invasions which may produce pre-cancerous cells; and 3) an anti-bacterial effect that could be used as a functional preservative.

Raspberries are preferably supplied in embodiments of the invention as a frozen concentrate having a 7:1 or 8:1 water:raspberry ratio based upon current supplier preferences. Raspberry, fruit juice concentrate is preferably included in the dietary supplements according to the invention in a range by wet weight of from about 0 percent to about 5 percent, more preferably from about 0.5 percent to about 2 percent. It has been determined according to the: invention that the combination of raspberry and blueberry fruit concentrates is particularly advantageous. In this case it is preferred to include from about 0.5 percent to about 5 percent of each of raspberry and blueberry fruit concentrates. As with the other ingredients, raspberries can be supplied in other known forms.

Additionally, there is some data known in the field showing that effective antioxidant protection requires the ingestion of a variety of antioxidant entities. It is theorized that this is because the combination of the different antioxidant entities leads to synergistic effects that provide the greatest health benefits. Thus, according to one preferred aspect of the invention, several high ORAC value fruits are incorporated in the dietary supplements. In addition, specially formulated high-ORAC fruit extracts can be incorporated into embodiments of the invention to maximize the antioxidant effects of the dietary supplements. Such high-ORAC fruit extracts are preferably added in amount from about 0% to about 5% by wet weight of the dietary supplement and have an ORAC value of at least about 200.

In addition to antioxidant rich fruits, other high ORAC value foods, such as high ORAC value herbs and vegetables, can also be included in the herein disclosed dietary supplements. These include, by way of example only, kale, spinach, Brussels sprouts, alfalfa sprouts, broccoli florets, beets, and red bell peppers, and other high ORAC value herbs such as green tea that are well known in the art.

5. Fulvates

Optional components of the herein disclosed dietary supplements are fulvates. Fulvates are organic electrolytes created by soil microbes that help break down organic material to make it available again for use by living plants. Scientists postulate that fulvates also play a vital role in providing essential nutrients and trace minerals for use by the human body, turning inorganic mineral elements into readily absorbable and bioavailable charged nutrients. After transporting their load of ionized minerals and nutrients to body cells where they can be converted into energy, filvates exit the cells. As they exit, they bind to any toxic heavy metals that may exist in the cytoplasm of the cell. Thus, Fulvates serve a dual role within the body—they deliver electrical energy, minerals and other nutrients to the body and clear out toxins, energy depleted nutrients and exhausted minerals from the cell. In addition, by increasing the bioavailiability and abosoprtion of minerals, fulvates enhance skeletal health.

Fulvates can be added to the dietary supplements in several forms, including by way of example only, a humic shale extract that includes a solution of fulvic acid and water. Fulvates are preferably supplied to embodiments of the invention in a range of from about 0 percent to about 1 percent by dry weight.

6. Preservatives

Although dietary supplements may be formulated to have the advantage of being artificial preservative free, it is of course contemplated that there may arise circumstances such as marketing or regulatory situations where the use of such preservatives is desired or even required. Accordingly, both natural and artificial preservatives may be used with the embodiments of the invention, including for example, potassium sorbate, sodium benzoate, methylparaben, natamax, and other preservatives that are known in the art or will be made known or developed hereafter.

In addition, compositions formed from Luo Han Guo (*Momordica grosvenori*) extract can be used as an organic preservative. The varieties of fruit known as Luo Han Guo come from the family Cucurbitaceae, tribe Jollifieae, subtribe Thladianthinae, genus *Siraitia* and include the genus/species *S. grosvenori*, *S. siamensis*, *S. silomaradjae*, *S. sikkimensis*, *S. africana*, *S. borneensis*, and *S. taiwaniana*. The Chinese plant *S. grosvenori*, or *Momordica grosvenori*, is referred to as Luo Han Guo in most Chinese Provinces, called Rakanka in Japan, and also known as Chinese Bitter Melon. Other common names for *M. grosvenori* include Lo Han Kuo, Arhat Fruit, and Fructus Momordicae. Although the fruits and leaves of the principal cultivated varieties have been described as showing striking differences in shape and color of the fruit and leaves, they are generally included together in China. Therefore, the fruit of the above plant varieties will be herein collectively referred to as "*Momordica*."

Traditionally, *Momordica* fruits are dried and stored in the dry state until used. The dried fruits are used whole, as liquid extracts, or in powdered or block forms. The powdered fruit form is often preferred because it is less expensive, less prone to problems with microbial growth, does not require refrigeration, is easier to transport, and has a longer shelf life. In one embodiment of the invention, the powder *Momordica* extract used in embodiments of the invention is supplied as an 80% mogrosides powder. The amount of *Momordica* that is used in embodiments of the invention varies depending on the concentration of various other ingredients in the dietary supplements.

7. Sweeteners

Sweeteners can be present in embodiments of the invention from various sources. For example, traditional sweeteners such as fructose and corn syrup can be used. Sweetness can also be provided from sugars that are present in other ingredients such as fruit juices.

In addition, although *Momordica* is preferably used at relatively low levels as a preservative in embodiments of the invention, *Momordica* can also be used at sufficiently higher levels in some embodiments such that it also acts as a sweetener. *Momordica* is of great interest to diabetics, to people watching their calorie intake, and in dental health. This is due in large part to the triterpene glycosides which act as non-caloric sweeteners in *Momordica*, also known as mogrosides. Recent reports are of particular interest because they show that mogrosides prevent LDL oxidation (a potential therapy for atherogenic disease) and are anti-cariogenic to teeth. A dental laboratory study clearly demonstrated two mechanisms of action against tooth decay. Firstly, *Momordica* does not provide a growth medium for Streptococcus mutans (the most common dental pathogen), like simple sugars (sucrose, glucose, and fructose). Secondly *Momordica* physically impairs *S. mutans* from adhering to hard surfaces.

8. Other

Preferably, the herein disclosed dietary supplements will include one or more additional well known components. For example, fructoligosaccharides such as Inulin can be added to boost mineral absorption and support healthy bacteria in the intestinal system. Amino acids can also be added from sources such as soy protein isolate and other nutrient-rich ingredients such as rice, Spirulina and kelp can be added as well.

In addition, one or more stabilizers such as maltodextrin can be included in a range from about 0% to 0.5% by dry weight of the dietary supplement.

Similarly, although not required, both additional natural and artificial flavoring ingredients may also be used. Examples of such flavoring ingredients include lemon juice flavoring, stevia, agave nectar, sucralose, corn syrup, and other sweeteners or flavorings that are known in the art or will be made known or developed hereafter.

In addition, the herein disclosed supplements will preferably have a pH value within a range from about 2.3 to about 3.9. Thus, citric acid, for example, may be added included in a range from about 0 percent to about 3 percent by dry weight of the dietary supplements to affect the pH of the dietary supplements as desired.

Colorants, such as for example, carmine and beet juice powder can also be optionally included to provided a desired color.

The largest single ingredient in juice based dietary supplements is water. The quantity of water in the present dietary supplements is calculated to be the amount necessary to reconstitute the fruit concentrates and provide the desired dilution for the dietary supplements. Typically, the amount of water in the dietary supplements will range from about 50% to about 95% by wet weight percent.

The following examples are given to illustrate the present invention, and are not intended to limit the scope of the invention.

EXAMPLES

Dietary supplement formulations were prepared with the compositions as presented in the following Examples 1-4.

Example 1

| Ingredients | Wet Percent | Dry Percent |
|---|---|---|
| Water | 65.33728% | — |
| Fructose | 14.60634% | 42.13847% |
| Fulvic Acid Solution | 10.00000% | 28.84944% |
| Blueberry Juice Concentrate | 2.00000% | 5.76989% |
| Citric Acid | 1.66666% | 4.80822% |
| Calcium Lactate | 1.30666% | 3.76964% |
| Raspberry Juice Concentrate | 1.00000% | 2.88494% |
| Beet Juice Powder | 0.66666% | 1.92328% |
| Calcium Chloride | 0.61236% | 1.76662% |
| Magnesium Chloride | 0.61236% | 1.76662% |
| Magnesium Citrate | 0.58666% | 1.69248% |
| Natural Flavors | 0.33334% | 0.96167% |
| Ascorbic Acid | 0.33300% | 0.96069% |
| Potassium Chloride | 0.22590% | 0.65171% |
| Fructooligosaccharides (Inulin) | 0.16666% | 0.48080% |
| High ORAC Fruit Extract | 0.13334% | 0.38468% |
| Sodium Benzoate | 0.11620% | 0.33523% |
| Soy Protein Isolate | 0.06666% | 0.19231% |
| Biotin | 0.03734% | 0.10772% |
| Vitamin B12 | 0.02622% | 0.07564% |
| Carmine | 0.02500% | 0.07212% |
| Maltodextrin | 0.02500% | 0.07212% |
| Niacinamide | 0.02246% | 0.06480% |
| Zinc Citrate | 0.01560% | 0.04501% |
| Thiamin Mononitrate | 0.01466% | 0.04229% |
| Riboflavin | 0.01126% | 0.03248% |
| FerrouseSulfate | 0.00986% | 0.02845% |
| Pyridoxine Hydrochloride | 0.00846% | 0.02441% |
| Folic Acid | 0.00740% | 0.02135% |
| Sea Salt | 0.00666% | 0.01921% |
| Copper Gluconate | 0.00598% | 0.01725% |
| Manganese Sulfate | 0.00547% | 0.01578% |
| d-Calcium Pantothenate | 0.00426% | 0.01229% |
| Sodium Selenite | 0.00245% | 0.00707% |
| Potassium Iodide | 0.00094% | 0.00271% |

-continued

| Ingredients | Wet Percent | Dry Percent |
|---|---|---|
| Sodium Molybdate | 0.00082% | 0.00237% |
| Chromium Chloride | 0.00008% | 0.00023% |
| Total | 100.00000% | 100.00000% |

Example 2

| Ingredients | Wet Percent | Dry Percent |
|---|---|---|
| Purified Water | 71.0250% | |
| Humic Shale Extract (Fulvic Acid) | 10.0000% | 34.5125% |
| Fructose | 6.6669% | 23.0090% |
| Corn Syrup | 3.0000% | 10.3538% |
| Blueberry Juice Concentrate | 2.0000% | 6.9025% |
| Calcium Lactate Pentahydrate | 1.5334% | 5.2921% |
| Raspberry Juice Concentrate | 1.0000% | 3.4513% |
| Citric Acid | 1.0000% | 3.4513% |
| Magnesium Sulfate | 0.7334% | 2.5310% |
| Beet Juice Powder | 0.6667% | 2.3009% |
| Natural Flavors | 0.4000% | 1.3805% |
| Ascorbic Acid | 0.3080% | 1.0630% |
| Potassium Chloride | 0.2667% | 0.9204% |
| Niacinamide | 0.2200% | 0.7593% |
| Inulin | 0.1667% | 0.5752% |
| Mixed Tocopherols: d-α Tocopherol, d-β Tocopherol, d-δ Tocopherol, d-γ Tocopherol | 0.1600% | 0.5522% |
| Sea Salt | 0.1067% | 0.3681% |
| Sodium Chloride-decreased Brine (Saline Lake) | 0.1000% | 0.3451% |
| Kelp | 0.0667% | 0.2301% |
| Soy Protein Isolate (Non-GMO) | 0.0667% | 0.2301% |
| Sodium Benzoate | 0.0600% | 0.2071% |
| Riboflavin | 0.0447% | 0.1542% |
| Cyanocobalamin | 0.0440% | 0.1519% |
| Pyridoxine Hydrochloride | 0.0367% | 0.1265% |
| Spirulina | 0.0333% | 0.1150% |
| Strawberry Extract | 0.0267% | 0.0920% |
| Elderberry Extract | 0.0267% | 0.0920% |
| Green Tea Extract | 0.0267% | 0.0920% |
| Wild Blueberry Extract | 0.0267% | 0.0920% |
| Orange Extract | 0.0267% | 0.0920% |
| Vitamin A Palmitate | 0.0267% | 0.0920% |
| Carmine | 0.0250% | 0.0863% |
| Maltodextrin | 0.0250% | 0.0863% |
| Momordica (*Siraitia grosvenori*) Extract | 0.0250% | 0.0863% |
| Thiamine Mononitrate | 0.0233% | 0.0805% |
| Cholecalciferol | 0.0147% | 0.0506% |
| Ferrous Sulfate | 0.0100% | 0.0345% |
| Folic Acid | 0.0074% | 0.0255% |
| d-Calcium Pantothenate | 0.0043% | 0.0147% |
| Silicone Resin | <4 ppm | |
| Total | 100.0000% | 100.00000% |

Example 3

| Ingredients | Wet Percent | Dry Percent | Amount Per Serving (15 g) |
|---|---|---|---|
| Purified Water | 81.0250% | | 12.155 g |
| Fructose | 6.6669% | 35.1350% | 1.000 g |
| Corn Syrup | 3.0000% | 15.8103% | 0.450 g |
| Blueberry Juice Concentrate | 2.0000% | 10.5402% | 0.300 g |
| Calcium Lactate Pentahydrate | 1.5334% | 8.0810% | 0.230 g |
| Raspberry Juice Concentrate | 1.0000% | 5.2701% | 0.150 g |
| Citric Acid | 1.0000% | 5.2701% | 0.150 g |
| Magnesium Sulfate | 0.7334% | 3.8648% | 0.110 g |
| Beet Juice Powder | 0.6667% | 3.5135% | 0.100 g |
| Natural Flavors | 0.4000% | 2.1081% | 0.060 g |
| Ascorbic Acid | 0.3080% | 1.6232% | 0.046 g |
| Potassium Chloride | 0.2667% | 1.4054% | 0.040 g |
| Niacinamide | 0.2200% | 1.1595% | 0.033 g |
| Inulin | 0.1667% | 0.8784% | 0.025 g |
| Mixed Tocopherols: d-α Tocopherol, d-β Tocopherol, d-δ Tocopherol, d-γ Tocopherol | 0.1600% | 0.8432% | 0.024 g |
| Sea Salt | 0.1000% | 0.5270% | 0.015 g |
| Mineral Complex (Potassium Chloride, Magnesium Chloride, Sodium Chloride) | 0.1000% | 0.5270% | 0.015 g |
| Kelp | 0.0667% | 0.3513% | 0.010 g |
| Soy Protein Isolate (Non-GMO) | 0.0667% | 0.3513% | 0.010 g |
| Sodium Benzoate | 0.0600% | 0.3162% | 0.009 g |
| Riboflavin | 0.0447% | 0.2354% | 0.007 g |
| Cyanocobalamin | 0.0440% | 0.2319% | 0.007 g |
| Pyridoxine Hydrochloride | 0.0367% | 0.1932% | 0.006 g |
| Spirulina | 0.0333% | 0.1757% | 0.005 g |
| Strawberry Extract | 0.0267% | 0.1405% | 0.004 g |
| Elderberry Extract | 0.0267% | 0.1405% | 0.004 g |
| Green Tea Extract | 0.0267% | 0.1405% | 0.004 g |
| Wild Blueberry Extract | 0.0267% | 0.1405% | 0.004 g |
| Orange Extract | 0.0267% | 0.1405% | 0.004 g |
| Vitamin A Palmitate | 0.0267% | 0.1405% | 0.004 g |
| Carmine | 0.0250% | 0.1318% | 0.004 g |
| Maltodextrin | 0.0250% | 0.1318% | 0.004 g |
| Momordica (*Siraitia grosvenori*) Extract | 0.0250% | 0.1318% | 0.004 g |
| Thiamine Mononitrate | 0.0233% | 0.1230% | 0.004 g |
| Cholecalciferol | 0.0147% | 0.0773% | 0.002 g |
| Ferrous Sulfate | 0.0100% | 0.0527% | 0.001 g |
| Folic Acid | 0.0074% | 0.0390% | 0.001 g |
| d-Calcium Pantothenate | 0.0043% | 0.0225% | 0.001 g |
| Silicone Resin | <4 ppm | | <0.6 ppm |
| Total Weight | 100.0000% | 100.0000% | 15.000 g |

Example 4

| Ingredients | Wet Percent | Dry Percent | Amount Per Serving (15 g) |
|---|---|---|---|
| Water | 75.3673% | | 11.3051 |
| Fructose | 14.6063% | 59.2965% | 2.1910 |
| Blueberry Juice Concentrate | 2.0000% | 8.1193% | 0.3000 |
| Citric Acid | 1.6667% | 6.7660% | 0.2500 |
| Calcium Lactate | 1.3067% | 5.3046% | 0.1960 |
| Raspberry Juice Concentrate | 1.0000% | 4.0596% | 0.1500 |
| Beet Juice Powder | 0.6667% | 2.7064% | 0.1000 |
| Calcium Chloride | 0.6124% | 2.4860% | 0.0919 |
| Magnesium Chloride | 0.6124% | 2.4860% | 0.0919 |
| Magnesium Citrate | 0.5867% | 2.3816% | 0.0880 |
| Natural Flavors | 0.3333% | 1.3532% | 0.0500 |
| Ascorbic Acid | 0.3330% | 1.3519% | 0.0500 |
| Potassium Chloride | 0.2259% | 0.9171% | 0.0339 |

-continued

| Ingredients | Wet Percent | Dry Percent | Amount Per Serving (15 g) |
|---|---|---|---|
| Fructooligosaccharides (Inulin) | 0.1667% | 0.6766% | 0.0250 |
| High ORAC Fruit Extract | 0.1333% | 0.5413% | 0.0200 |
| Sodium Benzoate | 0.1162% | 0.4717% | 0.0174 |
| Soy Protein Isolate | 0.0667% | 0.2706% | 0.0100 |
| Biotin | 0.0373% | 0.1516% | 0.0056 |
| Vitamin B12 | 0.0262% | 0.1064% | 0.0039 |
| Niacinamide | 0.0225% | 0.0912% | 0.0034 |
| Zinc Citrate | 0.0156% | 0.0633% | 0.0023 |
| Thiamin Mononitrate | 0.0147% | 0.0595% | 0.0022 |
| Riboflavin | 0.0113% | 0.0457% | 0.0017 |
| Carmine | 0.0100% | 0.0406% | 0.0015 |
| Maltodextrin | 0.0100% | 0.0406% | 0.0015 |
| Ferrous Sulfate | 0.0099% | 0.0400% | 0.0015 |
| Pyridoxine Hydrochloride | 0.0085% | 0.0343% | 0.0013 |
| Folic Acid | 0.0074% | 0.0300% | 0.0011 |
| Sea Salt | 0.0067% | 0.0270% | 0.0010 |
| Copper Gluconate | 0.0060% | 0.0243% | 0.0009 |
| Manganese Sulfate | 0.0055% | 0.0222% | 0.0008 |
| d-Calcium Pantothenate | 0.0043% | 0.0173% | 0.0006 |
| Sodium Selenite | 0.0025% | 0.0099% | 0.0004 |
| Potassium Iodide | 0.0009% | 0.0038% | 0.0001 |
| Sodium Molybdate | 0.0008% | 0.0033% | 0.0001 |
| Chromium Chloride | 0.0001% | 0.0003% | 0.0000 |
| Total Weight | 100.0000% | 100.0000% | 15.0000 g |

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A liquid mineral and vitamin dietary supplement, comprising, by wet weight of the dietary supplement:
14.6063% fructose, 2.0000% blueberry juice concentrate, 1.6667% citric acid, 1.3067% calcium lactate, 1.0000% raspberry juice concentrate, 0.6667% beet juice powder, 0.6124% calcium chloride, 0.6124% magnesium chloride, 0.5867% magnesium citrate, 0.3333% natural flavors, 0.3330% ascorbic acid, 0.2259% potassium chloride, 0.1667% fructooligosaccharides (inulin), 0.1333% high ORAC (Oxygen Radical Absorption Capacity) fruit extract, 0.1162% sodium benzoate, 0.0667% soy protein isolate, 0.0373% biotin, 0.0262% vitamin $B_{12}$, 0.0225% niacinamide, 0.0156% zinc citrate, 0.0147% thiamin mononitrate, 0.0113% riboflavin, 0.0100% or 0.025% carmine, 0.0100% or 0.025% maltodextrin, 0.0099% ferrous sulfate, 0.0085% pyridoxine hydrochloride, 0.0074% folic acid, 0.0067% sea salt, 0.0060% copper gluconate, 0.0055% manganese sulfate, 0.0043% d-calcium pantothenate, 0.0025% sodium selenite, 0.0009% potassium iodide, 0.0008% sodium molybdate, and 0.0001% chromium chloride.

2. The dietary supplement as defined in claim 1, wherein the ORAC level of the dietary supplement is from about 1,000 to about 48,800 μmole TE/100gm.

3. The dietary supplement as defined in claim 1, wherein the pH of the dietary supplement is from about 2.8 to about 3.6.

4. The dietary supplement as defined in claim 1, further comprising 10% fulvates by wet weight of the dietary supplement.

5. The dietary supplement as defined in claim 1, wherein the dietary supplement is prepared by a process that includes ultra high temperature pasteurization.

6. The dietary supplement as defined in claim 1, further comprising Momordica extract in an amount sufficient to inhibit bacterial growth and extend the shelf life of the dietary supplement.

7. The dietary supplement as defined in claim 6, wherein the Momordica extract is present as an 80% mogrosides powder.

8. The dietary supplement as defined in claim 1, wherein the carmine comprises 0.025% by wet weight of the dietary supplement and the maltodextrin comprises 0.025% by wet weight of the dietary supplement.

9. A liquid mineral and vitamin dietary supplement, comprising, by wet weight of the dietary supplement:
6.6669% fructose, 3.0000% corn syrup, 2.0000% blueberry juice concentrate, 1.5334% calcium lactate pentahydrate, 1.0000% raspberry juice concentrate, 1.0000% citric acid, 0.7334% magnesium sulfate, 0.6667% beet juice powder, 0.4000% natural flavors, 0.3080% ascorbic acid, 0.2667% potassium chloride, 0.2200% niacinamide, 0.1667% inulin, 0.1600% mixed tocopherols (d-α tocopherol, d-β tocopherol, d-δtocopherol and d-γ tocopherol), 0.1000% sea salt, 0.0667% kelp, 0.0667% soy protein isolate, 0.0600% sodium benzoate, 0.0447% riboflavin, 0.0440% cyanocobalamin, 0.0367% pyridoxine hydrochloride, 0.0333% spirulina, 0.0267% vitamin A palmitate, 0.0250% carmine, 0.0250% maltodextrin, 0.0250% Momordica (siraitia grosvenori) extract, 0.0233% thiamine mononitrate, 0.0147% cholecalciferol, 0.0100% ferrous sulfate, 0.0074% folic acid, 0.0043% d-calcium pantothenate, and <4ppm silicone resin.

10. The dietary supplement as defined in claim 9, further comprising 0.1000% by wet weight of the dietary supplement a mineral complex, wherein the mineral complex includes each of potassium chloride, magnesium chloride, and sodium chloride.

11. The dietary supplement as defined in claim 9, further comprising 10% fulvates by wet weight of the dietary supplement.

12. The dietary supplement as defined in claim 9, further comprising 0.1000% by wet weight of the dietary supplement a sodium chloride-decreased brine (saline lake).

13. The dietary supplement as defined in claim 9, further comprising, by wet weight of the dietary supplement, one or more of 0.0267% of strawberry extract, 0.0267% of elderberry extract, 0.0267% of green tea extract, 0.0267% of wild blueberry extract or 0.0267% by wet weight of orange extract.

14. The dietary supplement as defined in claim 9, wherein the ORAC level of the dietary supplement is from about 1,000 to about 48,800 μmole TE/100gm.

15. The dietary supplement as defined in claim 9, wherein the pH of the dietary supplement ranges from about 2.8 to about 3.6.

16. A liquid mineral and vitamin dietary supplement, comprising, by wet weight of the dietary supplement:
10.0000% humic shale extract (fulvic acid), 6.6669% fructose, 3.0000% corn syrup, 2.0000% blueberry juice concentrate, 1.5334% calcium lactate pentahydrate, 1.0000% raspberry juice concentrate, 1.0000% citric acid, 0.7334% magnesium sulfate, 0.6667% beet juice powder, 0.4000% natural flavors, 0.3080% ascorbic acid, 0.2667% potassium chloride, 0.2200% niacinamide, 0.1667% inulin, 0.1600% mixed tocopherols (d-α tocopherol, d-β tocopherol d-δ tocopherol and d-γtocopherol), 0.1067% sea salt, 0.1000% sodium chloride-decreased brine (saline lake), 0.0667% kelp, 0.0667% soy protein isolate, 0.0600% sodium benzoate, 0.0447% riboflavin, 0.0440% cyanocobalamin, 0.0367% pyridoxine hydrochloride, 0.0333% spirulina, 0.0267% strawberry extract, 0.0267% elderberry extract, 0.0267% green tea extract, 0.0267% wild blueberry extract, 0.0267% orange extract, 0.0267% vitamin A palmitate, 0.0250% carmine, 0.0250% maltodextrin, 0.0250% Momordica (siraitia grosvenori) extract, 0.0233% thiamine mononitrate, 0.0147% cholecalciferol, 0.0100% ferrous sulfate, 0.0074% folic acid, 0.0043% d-calcium pantothenate, and <4ppm silicone resin.

17. The dietary supplement as defined in claim 16, further comprising, by weight of the dietary supplement, 0.1000% of a mineral complex, wherein the mineral complex includes each of potassium chloride, magnesium chloride, and sodium chloride.

18. The dietary supplement as defined in claim 16, wherein the ORAC level of the dietary supplement is from about 1,000 to about 48,800 µmole TE/100gm.

19. The dietary supplement as defined in claim 16, wherein the pH of the dietary supplement ranges from about 2.8 to about 3.6.

* * * * *

UNITED STATES PATENT AND TRADEMARK OFFICE
CERTIFICATE OF CORRECTION

PATENT NO. : 7,964,234 B2
APPLICATION NO. : 11/173611
DATED : June 21, 2011
INVENTOR(S) : Mower et al.

Page 1 of 1

It is certified that error appears in the above-identified patent and that said Letters Patent is hereby corrected as shown below:

Column 3
Line 20, change "filvates" to --fulvates--
Line 49, change "10,000μmole" to --10,000 μmole--

Column 6
Line 15, change "2,400.0 100%" to --2,400.0, 100%--

Column 8
Line 8, change "the: invention" to --the invention--
Line 45, change "filvates" to --fulvates--
Line 51, change "abosoprtion" to --absorption--

Column 10
Line 59, change "FerrouseSulfate" to --Ferrous Sulfate--

Column 14
Line 67, change "d-β tocopherol d-δ" to --d-β tocopherol, d-δ--
Line 67, change "d-γtoco-" to --d-γ toco- --

Signed and Sealed this
Twenty-second Day of November, 2011

David J. Kappos
*Director of the United States Patent and Trademark Office*